(12) United States Patent
Akinyemi et al.

(10) Patent No.: US 7,941,462 B2
(45) Date of Patent: May 10, 2011

(54) METHOD AND APPARATUS FOR CLASSIFICATION OF CORONARY ARTERY IMAGE DATA

(75) Inventors: Akinola Akinyemi, Edinburgh (GB); Sean Murphy, Edinburgh (GB); Ian Poole, Edinburgh (GB)

(73) Assignee: Toshiba Medical Visualization Systems Europe, Limited, Edinburgh (GB)

( * ) Notice: Subject to any disclaimer, the term of this patent is extended or adjusted under 35 U.S.C. 154(b) by 408 days.

(21) Appl. No.: 12/236,789

(22) Filed: Sep. 24, 2008

(65) Prior Publication Data

US 2010/0082692 A1 Apr. 1, 2010

(51) Int. Cl.
*G06F 7/00* (2006.01)
*G06F 17/30* (2006.01)
(52) U.S. Cl. ........................................ 707/803; 707/758
(58) Field of Classification Search .................. 707/803, 707/758
See application file for complete search history.

(56) References Cited

U.S. PATENT DOCUMENTS 7,722,663 B1 * 5/2010 Austin .......................... 623/1.22

FOREIGN PATENT DOCUMENTS

JP 2010-75693 * 4/2010

OTHER PUBLICATIONS

N. Ezquerra et al., "Model-Guided Labeling of Coronary Structure" IEEE Transactions on Medical Imaging, vol. 17, pp. 429-441, 1998.

* cited by examiner

*Primary Examiner* — Kuen S Lu
(74) *Attorney, Agent, or Firm* — Renner, Otto, Boisselle & Sklar, LLP

(57) ABSTRACT

A polyline tree representation of a coronary artery tree imaged in a volume data set is obtained, and its topology is extracted to give a topological representation indicating the relative positions of vessels in the tree. The topological representation is compared with a set of topological rules to find possible anatomical classifications for each vessel, and a set of candidate labeled polyline trees is generated by labeling the polyline tree with labels showing each combination of possible anatomical classifications. Each candidate labeled tree is filtered according to a set of geometric rules pertaining to spatial characteristics of vessels in arterial trees, and any labeled tree not satisfying the geometric rules is rejected A figure of merit is calculated for each remaining candidate by comparing features of the vessels measured from the polyline tree and from the volume data set with features of correctly classified vessels in other data sets to determine the probable correctness of the labeling of each candidate, and the candidate with the best figure of merit is selected as showing the proper classification of the vessels.

24 Claims, 4 Drawing Sheets

METHOD AND APPARATUS FOR CLASSIFICATION OF CORONARY ARTERY IMAGE DATA

BACKGROUND OF THE INVENTION

The present invention relates to a method and apparatus for automatic classification and labeling of images of arterial trees, in particular coronary arteries.

Modern medical image techniques such as magnetic resonance imaging (MRI) and computerised tomography (CT) generate highly detailed images of a patient's internal anatomy. The imaging apparatuses produce so-called volume data sets comprising three-dimensional arrays of volume elements (voxels) where each voxel has a value indicating the value of some physical attribute of a corresponding small volume of the patient, where that attribute is measured by the imaging apparatus. For example, in CT this is the Hounsfield unit, which represents the attenuating ability of the patient's tissue to X-ray radiation.

Volume data sets require processing and manipulation by computer to render the data into a format which is useful and intelligible to medical personnel. For example, a two-dimensional image showing a slice through the volume of the data set can be produced. A further technique is that of segmenting, where the voxels corresponding to a particular organ or other anatomical structure are distinguished and separated from the surrounding voxels, for example by selecting contiguous voxels having values within a certain range. Images of the anatomical structure in isolation can then be displayed.

The coronary arterial tree is an example of such a structure which is frequently of medical interest. However, the arterial tree is a complex structure and its individual components may not be readily distinguishable on a displayed image. Therefore, it is useful if the image rendering process includes a classification procedure that can automatically identify and label the various parts. The labels can be displayed to the viewer to aid in procedures such as visual diagnosis, screening or training, and/or can be associated with the data set for use in automated diagnostics software and the like.

Currently techniques for coronary artery labeling rely on the technique of graph matching [1, 2]. However, this approach suffers from the problem that graph matching does not exploit the full knowledge about the coronary anatomy. Also, the cost functions used in previously proposed labeling methods do not consider the multivariate structure of the feature space. Therefore, there is a need for an alternative technique for automated arterial labeling.

SUMMARY OF THE INVENTION

Accordingly, a first aspect of the present invention is directed to a method of automatically classifying anatomical features shown in a medical image volume data set, the method comprising: obtaining a polyline tree comprising a plurality of connected points in the data set corresponding to the centrelines of vessels in an arterial tree imaged in the data set, each vessel in the arterial tree being represented by a segment in the polyline tree; forming a topological representation of the polyline tree which indicates the relative generational positions of the segments within the polyline tree; comparing the topological representation with a set of topological rules specifying anatomically permissible relative generational positions of vessels in an arterial tree to identify feasible anatomical classifications for the vessels represented by each segment in the polyline tree; generating a set of candidate labeled polyline trees by associating labels representing the identified anatomical classifications with the corresponding segments in the polyline tree, each candidate labeled polyline tree being one combination of the identified feasible anatomical classifications; comparing each candidate labeled polyline tree with a set of geometric rules specifying anatomically permissible spatial attributes of vessels in an arterial tree which can be determined from a polyline representation and rejecting any candidate having one or more labels representing vessels which do not comply with the geometric rules; calculating a figure of merit for each remaining candidate labeled polyline tree by comparing features of the vessels represented in the polyline tree with known features of vessels in the anatomical classes indicated by the labels associated with the segments representing the vessels to determine a probability of the correctness of the labels in each candidate, the figure of merit reflecting the probability; and identifying the candidate labeled polyline tree having the best figure of merit.

This method provides an accurate and computationally efficient technique for automatically classifying and labeling coronary artery image data. A correctly labeled image can thereby be presented to a user or a correctly classified data set can be exported to diagnostics software with little or no need for intervention by a clinician or other medical staff. Typically only a quick verification of the correctness of the labels is required, and in most cases no or very few changes are needed. This can increase the speed of handling if a large number of patient images are required to be processed.

The number of differently classified or named vessels in the coronary artery tree is sufficiently large that there is an enormous number of possible combinations of labels. Only one of these is correct, but many of the others are feasible according to different methods of identifying vessel types. To consider every feasible classification in detail to identify the correct classification would require a lot of computation time and power. The present invention proposes to produce the correct classification by eliminating the majority of the possible label combinations using filtering according to different rules sets to leave a small number of the most feasible combinations for closer consideration. Thus, the imaged arterial tree is subjected to a set of topological rules as a first stage in reducing the amount of possible classifications, and then subjected to a set of geometric rules to remove further candidate classifications. These final remaining candidates are processed by calculation of a figure of merit derived by comparison of features of the imaged arterial tree with features in known correctly classified trees to identify the correct classification as that with the best figure of merit.

A benefit of using topological and geometric rules for candidate elimination is that the relevant features defined by these rule sets can be identified from a simple polyline tree representation of the full three-dimensional arterial tree image. Thus the classification processing can be conducted using a much smaller quantity of data than the alternative of handling the full image volume data set or even a segmented version of the arterial tree image. Thus, the computational cost is further reduced.

The form of the topological representation can be selected as convenient. One option is a predecessor array.

The vessel classification indicated by the final labeled polyline tree identified by the method may be employed as required. The classified polyline tree itself may be of further use, or it may be preferred to transfer the labels to the original image data. Therefore, the method may further comprise associating the labels from the identified candidate with the corresponding vessels in the imaged arterial tree to indicate the classification of the vessels.

In some embodiments, calculating a figure of merit for each remaining candidate labeled polyline tree may comprise: measuring a set of preselected features of each vessel represented in the polyline tree; combining the measurements for each vessel to calculate a feature vector for each vessel; and, for each candidate labeled polyline tree, comparing the calculated feature vector for each vessel with one or more predetermined parameters derived from features of the anatomical class of vessel indicated by the label associated with the segment representing that vessel to determine a probability that each label is correct, and combining the probabilities within each candidate labeled polyline tree to produce a figure of merit for each candidate.

For example, the predetermined parameters may comprise a mean feature vector and a variance-covariance matrix for the anatomical class of vessel.

Any suitable measure of probability can be employed, but it has been found that log-likelihoods give good results. Therefore, in some embodiments, comparing the calculated feature vector for each vessel with a predetermined mean feature vector and a variance-covariance matrix to determine a probability comprises calculating a log-likelihood.

Then, combining the probabilities to produce a figure of merit may comprise summing the log-likelihoods for every labeled segment in the candidate labeled polyline tree.

The predetermined mean feature vectors may be the mean values of a plurality of feature vectors calculated for correctly classified vessels in arterial trees imaged in other data sets, and the variance-covariance matrices may be calculated for correctly classified vessels in arterial trees imaged in the other data sets. This mitigates the effects of any anatomical peculiarities or errors in the images which could otherwise adversely affect the feature comparison. The use of mean values obtained from a plurality of data sets in effect produces standardised feature vectors reflecting "average" arterial vessel structures.

In alternative embodiments, comparing the calculated feature vector for each vessel with one or more parameters derived from features of the anatomical class of vessel indicated by the label associated with the segment representing the vessel may comprise use of a K-nearest neighbour technique, or use of Baysian histograms.

While many vessel features relevant for the feature vectors can be obtained directly from the polyline tree, further enhancement can be obtained by also considering features obtainable from the original image data, such as vessel diameter. Therefore, in one embodiment, measuring the preselected features for each vessel comprises measuring features from the polyline tree and from the data set.

A second aspect of the present invention is directed to a system for automatically classifying anatomical features shown in a medical image volume data set, the system comprising: a topology extractor module operable to receive a polyline tree comprising a plurality of connected points in the data set corresponding to the centrelines of vessels in an arterial tree imaged in the data set, each vessel in the arterial tree being represented by a segment in the polyline tree, and to form a topological representation of the polyline tree which indicates the relative generational positions of the segments within the polyline tree; a set of topological rules specifying anatomically permissible relative generational positions of vessels in an arterial tree; a set of labels representing anatomical classifications of arterial vessels; a topology checker module operable to compare the topological representation with the set of topological rules to identify feasible anatomical classifications for the vessels represented by each segment in the polyline tree and to generate a set of candidate labeled polyline trees by associating labels from the label set which represent the identified anatomical classifications with the corresponding segments in the polyline tree, each candidate labeled polyline tree being one combination of the identified feasible anatomical classifications; a set of geometric rules specifying anatomically permissible spatial attributes of vessels in an arterial tree which can be determined from a polyline representation; a geometry checker module operable to compare each candidate labeled polyline tree with the set of geometric rules and reject any candidate having one or more labels representing vessels which do not comply with the geometric rules; and a merit figure module operable to calculate a figure of merit for each remaining candidate labeled polyline tree by comparing features of the vessels represented in the polyline tree with known features of vessels in the anatomical classes indicated by the labels associated with the segments representing the vessels to determine a probability of the correctness of the labels in each candidate, the figure of merit reflecting the probability, and to identify the candidate labeled polyline tree having the best figure of merit.

The merit figure module may perform the comparing by comparing feature vectors for the vessels represented in the polyline tree with predetermined mean feature vectors and variance-covariance matrices for vessels of the anatomical class indicated by the labels of the candidate trees. For this, the system may be further configured to obtain the mean feature vectors and variance-covariance matrices by "training" using known correctly classified arterial tree images or polyline trees. Therefore, the system may further comprise a feature extractor and classifier module operable to: measure sets of preselected features of correctly classified vessels in a plurality of polyline trees representing a plurality of imaged arterial trees; combine the measurements for each vessel to calculate a feature vector for each vessel; and calculate a mean feature vector and a variance-covariance matrix for each anatomical class of vessel from the calculated feature vectors; and memory operable to store the mean feature vectors and variance-covariance matrices for retrieval by the merit figure module when calculating figures of merit.

A third aspect of the present invention is directed to a medium storing a computer program product operable to cause a computer system to implement the method according to the first aspect.

BRIEF DESCRIPTION OF THE DRAWINGS

For a better understanding of the invention and to show how the same may be carried into effect reference is now made by way of example to the accompanying drawings in which.

Figure 1:
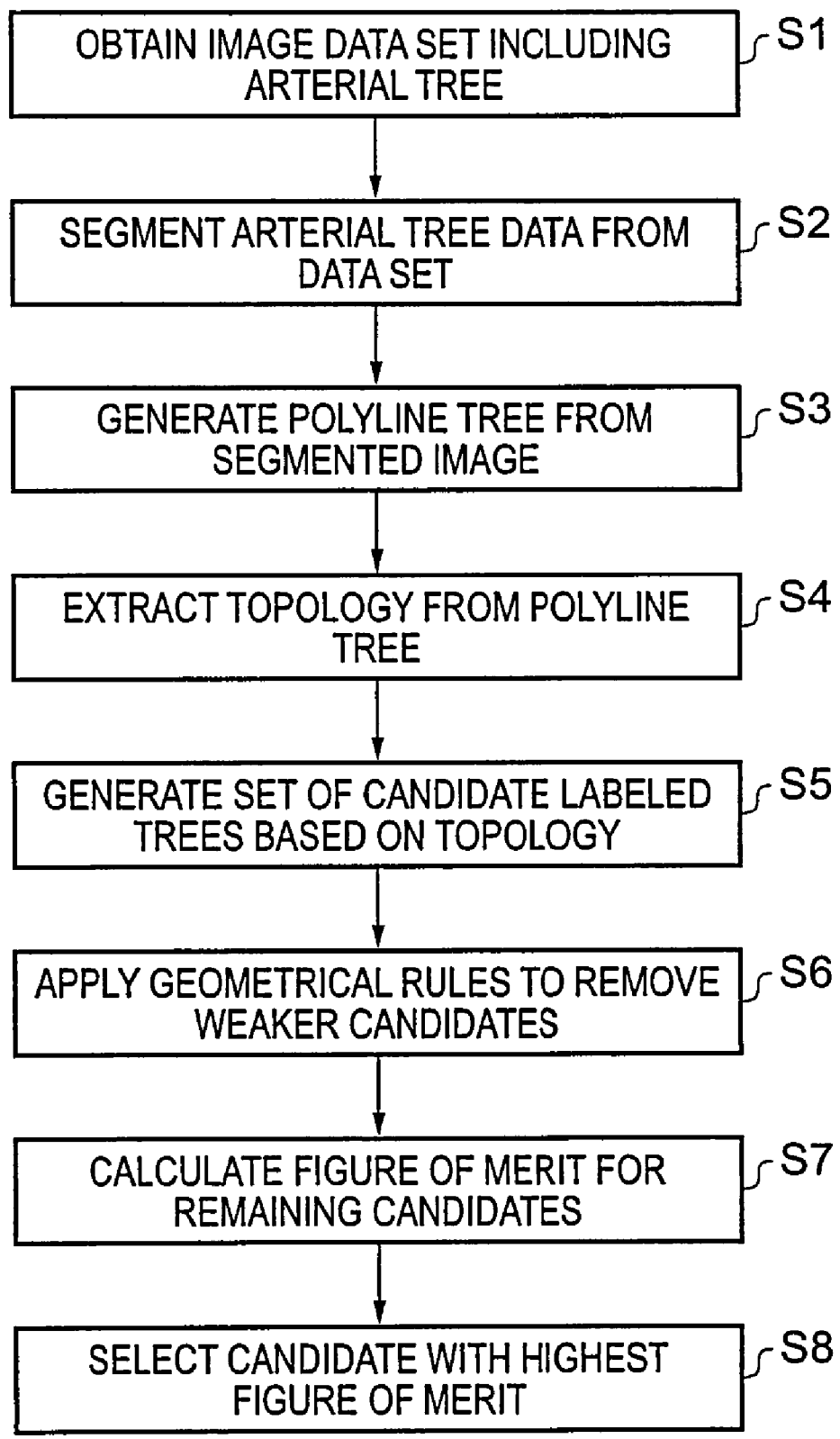
FIG. 1 shows a flow chart representing steps in an embodiment of a method according to the present invention.

While the invention is susceptible to various modifications and alternative forms, specific embodiments are shown by way of example in the drawings and are herein described in detail. It should be understood, however, that the drawings and detailed description are not intended to limit the invention to the particular form disclosed, but on the contrary, the invention is to cover all modifications, equivalents and alternatives falling within the spirit and scope of the present invention as defined in the appended claims.

DETAILED DESCRIPTION

The human coronary arterial tree comprises the left and right main coronary arteries which branch off from the ascending aorta, and a number of successively smaller vessels which branch off from the main arteries. The present invention seeks to provide a technique for automatic classification and labeling of the various vessels included in a three-dimensional image of the arterial structure. The technique uses filtering based on topological and geometrical parameters to obtain a set of potentially correctly labeled candidates for an imaged arterial tree. A figure of merit is calculated for each member of the set, and the candidate with the best figure of merit is output as the final labeled tree.

FIG. 1 shows a flow chart indicating the steps in an example embodiment of this technique.

Step S1 requires that a volume data set be obtained which includes the arterial tree of interest. The data may be recorded using any suitable imaging technique. Then, in step S2, the arterial tree data is segmented from the volume data set, so that only the data of interest is retained.

Once the arterial tree data is obtained, in step S3 a polyline tree of the arterial structure is generated from the segmented image data. Note that the method shown in FIG. 1 is an example only. The method may begin at any of steps S1, S2 or S3, depending on whether the relevant image data has been measured on a previous occasion and stored for later use with or without being segmented (for example in a picture archiving and communication system (PACS) in a hospital), and with or without generation of the polyline tree. Alternatively, it may be possible to generate the polyline tree directly from the volume data set without the need for segmentation.

Then, in step S4, the topology of the arterial tree is extracted from the polyline tree. The topology indicates the relative positions of the various vessels within the arterial tree, in particular in terms of the generational relationships between the vessels.

A pool of labels representing each of the vessels comprised within an arterial tree is provided, together with rules governing the topological relationships between different vessels and vessel types (classifications). In step S5, this data is used to apply labels to the arterial tree according to the extracted topology. Since there are many vessels in the polyline tree and each vessel may comply with more than one rule, this process typically produces a set of candidate labeled trees, each of which is potentially correct or "legal" in terms of the topology of standard arterial anatomy.

In step S6, the set of candidates is reduced in size by considering the geometric features of the polyline tree and rejecting any candidate which is labeled in a way which contradicts the geometry of standard arterial anatomy. The standard geometry can be defined by a set of geometric rules.

In step S7, a figure of merit is calculated for each remaining candidate. The figure of merit is determined by comparison of features of each labeled vessel in the candidate polyline tree and of the original arterial tree data with features of known vessel types in previously correctly classified and labeled arterial tree images. A high level of correspondence produces a good figure of merit.

Finally, in step S8, the candidate having the best figure of merit is selected, and its labels can be assigned as labels for the arterial tree image data.

It would be possible to use the comparison of step S7 directly to determine the appropriate labels for the vessels in the tree of interest. However, a typically tree contains many vessels, and comparing the features of every vessel with the features of each possible classification for a vessel to determine the best match would be very computationally intensive. Therefore, the present invention proposes to reduce the processing by filtering the total number of possible labeled trees (in which any individual vessel could in theory be classified and labeled as any vessel type) according to topological and geometrical characteristics before comparing features with known features. For any individual vessel, the filtering reduces the possible correct labels to a few at most, so that the feature comparison for each vessel need only be carried out against the few vessel types represented by those labels. The total time and computational cost for classifying and labeling an arterial tree is thereby reduced.

The steps shown in FIG. 1 will be now be described in more detail, with reference to FIG. 2, which shows an embodiment of a system for implementing the method of FIG. 1.

The lower half of FIG. 2 will be described first. This part of the system comprises a topology extractor 10, which receives an un-labeled polyline tree 1 as an input, and produces the topology of that tree as an output. The topology is supplied to a label generator 20, which also receives data from a label pool 22, and operates with a topology checker 24 to generate a set of labeled candidate trees 2 which are labeled in a topologically-feasible manner. This set of candidates 2 is supplied to a geometry checker 30, which filters the candidates according to geometrical rules, and produces a set of geometrically-feasible labeled candidate trees 3 smaller in size than the set of topologically-feasible labeled trees 2. This reduced set 3 is passed to a merit function module 40 which calculates a figure of merit for each candidate tree, selects the candidate with the best figure of merit, and outputs this candidate so that the system overall produces a single labeled tree 4.

As its input, the system takes an unlabeled polyline tree 1. A polyline is a data structure used to represent lines or curves in three-dimensional space. A polyline comprises a set of points, each represented by x, y and z co-ordinates indicating its position in space (in the present case, its position within the volume data set), which collectively make up a line, a curve or a closed curve. In the present context, a polyline is a collection of points along the centreline of a vessel or artery within an arterial tree, and a polyline tree is a collection of the polylines (or centrelines) of the individual arteries or vessels that make up the coronary artery tree or coronary vasculature. The polyline tree is therefore a data structure used to represent the whole arterial tree, each segment of the polyline tree representing a vessel. The polyline tree may be thought of as a "skeleton" of the coronary arterial tree, representing the lengths, branching angles, curvature and connectivity of the vessels in the tree, but not their widths.

Any technique for producing the polyline tree of an arterial tree of interest may be used. The centrelines of the vessels may be tracked manually on a displayed image using a software system such as "VesselMetrix" (manufactured by Barco NV of Belgium). Alternatively, an automatic centreline tracking algorithm [3] (of which many are known) may be used to automatically extract the centrelines from the volume data set or the segmented arterial tree data.

For good classification results, the polyline tree may be extracted from the image data according to a protocol in which, for each class of vessel, a vessel is tracked along its centreline as a single vessel (ignoring all branches) from its start point until it becomes invisible, and the starting point of each branching vessel is made to coincide with a point on the centreline of the parent vessel.

Figure 3:
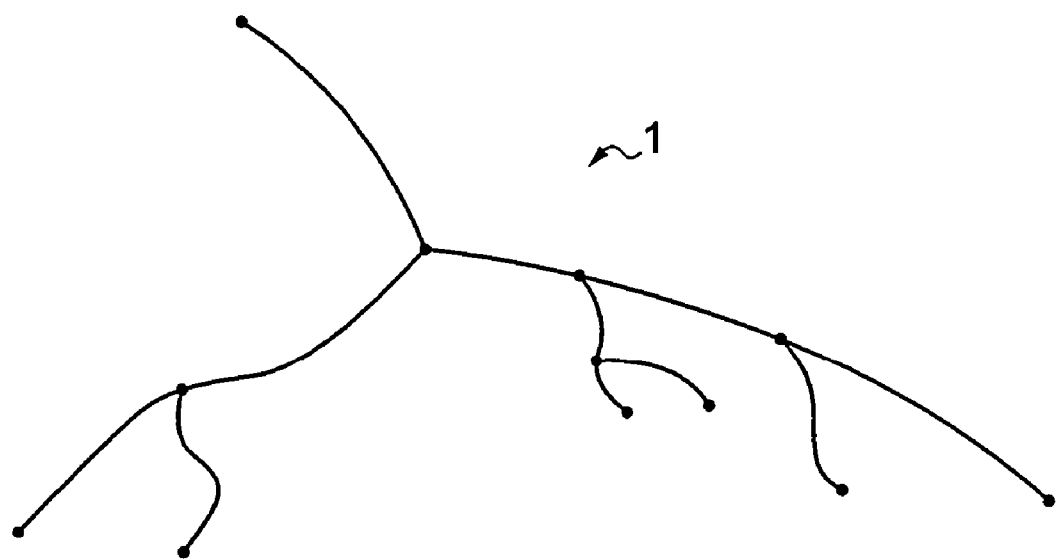
FIG. 3 shows an example of a polyline tree representing a coronary arterial tree.

FIG. 3 shows an example of an unlabeled polyline tree 1 representing a typical left main artery and its branches.

Figure 2:
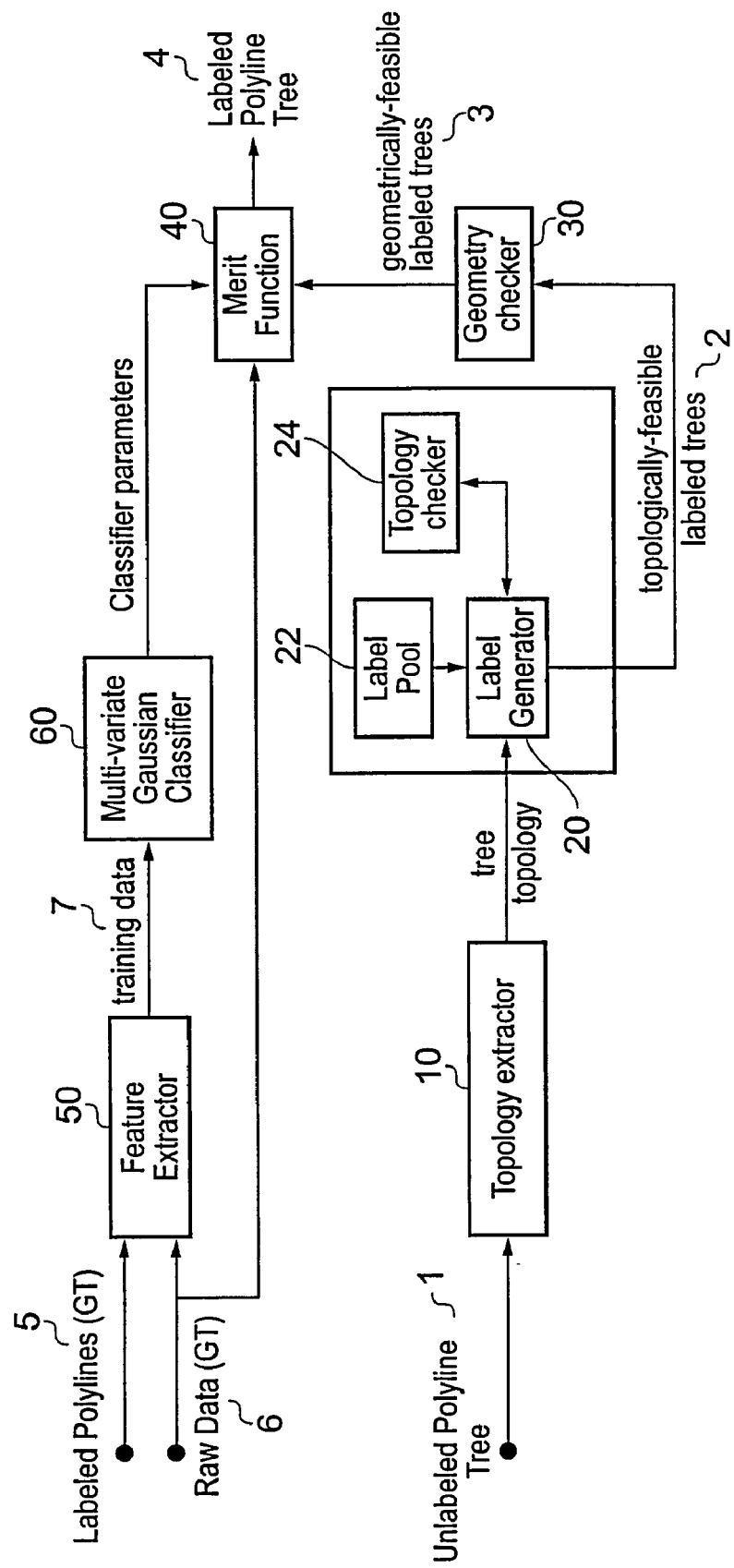
FIG. 2 shows a schematic representation of an embodiment of a system for implementing a method according to the present invention.

The polyline tree 1 representing the coronary artery tree of interest is input to the topology extractor 10 shown in FIG. 2. The topology extractor 10 analyses the polyline tree to extract topological data. The purpose of this is to obtain information regarding the structure of the unlabeled tree which is relevant to classifying the anatomy. The topological data is the topology of the vessels, and refers to the ordering of the different anatomical classes of vessels according to the tree structure of the coronary vasculature. Physical attributes of the vasculature such as length, curvature, diameter and the like can be disregarded for this purpose. Instead, the topological data represents the relative positions of each segment in the tree.

Any technique for determining the required topological data may be used. In one example, the topology extractor takes the inputted unlabeled polyline tree, performs a depth-first search on the polyline tree, and constructs a predecessor array [4] that depicts the topology of the polyline tree. A predecessor array is an N-length vector containing the relative positions of the segments in the original polyline tree. The array has the form of a branched tree structure branching from a root, and each root/branch corresponds to a vessel/segment in the polyline tree. The array preserves the topological information of the polyline tree regarding the level of each vessel within the tree and how many vessels branch from the root and each vessel, i.e. it reflects the position of each vessel relative to the other vessels, without indicating any physical structure. Using a predecessor array, the polyline tree can be represented simply as a list of positions of the vessel segments.

Figure 4:
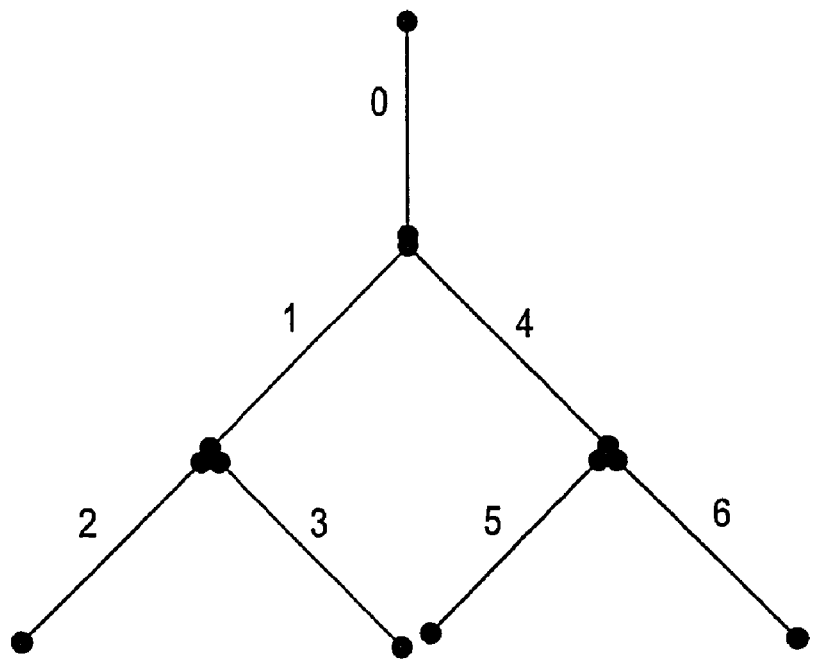
FIG. 4 shows an example of a predecessor array derived from a polyline tree as an example of a topological representation of a coronary arterial tree.

FIG. 4 shows an example of a predecessor array topological representation of a simple tree with seven vessels or segments. The seven segments are numbered from 0 (the root) to 6. The predecessor array can be represented numerically as {0,1,2,2,1,5,5}.

Other representations of the tree topology may be used if preferred.

The tree topology produced by the topology extractor 10 is provided to the label generator 20 and the topology checker 24, which operate to generate a set of candidate labeled trees.

The labels are selected from a label pool 22 which is accessible by the label generator 20. The label pool stores a set of labels comprising labels representing names for the vessels within a coronary arterial tree, a label being provided for each anatomical structure which it is desired to be able to identify or classify in an arterial tree of interest. The labels may take any form that is useful for the intended application of the finally labeled tree. For example, a pool of labels showing the conventional anatomical names and abbreviations for the various arterial vessels may be provided; this will be useful for an application in which a meaningfully labeled image of the arterial tree is presented to an observer. Such a pool will typically include the following labels:

Left main (LM)
Left anterior descending (LAD)
Left circumflex (LCX)
Left marginal (LMG)
Left Ramus-intermedius (LRI)
Left diagonal (LD)
Left/Right insignificant (LINSIG, RINSIG)—all vessels not required in the classification
Right coronary artery (RCA)
Right posterior descending artery (RPD)—not always present For enhanced versatility of the system, the label pool may include several sets of labels, each set comprising labels representing a different format of name. In this way, the label format most appropriate for the intended application of the labeled tree can be used.

The label generator 20 and topology checker 24 generate a set of labeled trees by considering the topology of the original unlabeled polyline tree as indicated by the predecessor array and assigning labels to the segments in the tree according to topological rules which govern the standard anatomy of coronary artery trees. The topological rules are pertinent to the syntactic structure of coronary arteries. The rules define the way in which each type or class of vessel in an arterial tree is anatomically connected to other vessels, in terms of the level or generation of the vessel within the tree and which vessels are in the previous or later generations (which vessel or type of vessel can be its parent; which vessels or type of vessels can be its children; which vessels or types of vessel can be its siblings; whether a vessel of a particular type can have a parent, sibling or child; how many siblings or children are permitted for a vessels of a particular type, etc.).

For each segment in the tree, its topological data is considered and every label in the label pool which complies with the topological rules met by that data is considered as a potentially correct or legal label for that segment. For many segments, there might be several vessels types into which the segment can be classified without breaking the topological rules, so several labels are potentially correct for these segments. In this way, a plurality of labeled polyline trees are generated, covering every combination of the legal labels identified for each segment.

An example set of topological rules may include some or all of the following:

For the left coronary tree:
  The root segment of the left coronary tree is the LM.
  LM cannot have any siblings.
  RCA, RPD and RINSIG are not permitted in the left tree.
  LAD can only be a child or LM or an extension of itself.
  LCX can only be a child of LM or an extension of itself.
  LD can only be a child of LAD or an extension of itself.
  LMG can only be a child of LCX or an extension of itself.
  LRI can only be a child of LM or an extension of itself.
  LRI can only occur in the middle of a trifurcation.
For the right coronary tree:
  Only RCA, RPD and RINSIG are permitted in the right tree.
  The root segment must be RCA
  RCA can only be a child of RCA or an extension of itself.
  RPD can only be a child of RCA or an extension of itself.
For both left and right sides:
  Sibling branches cannot be in the same class.
  All RCA, RPD, LAD, LCX and LM segments must be continuous.
  Any child branch of an INSIGNIFICANT segment must be INSIGNIFICANT.

The topological rules are stored in memory accessible by the topology checker, which may be external memory or memory located within the topology checker, depending on the hardware and/or software configuration used to implement the system.

The topology checker 24 analyses the topology of the unlabeled tree according to the extracted tree topology from the topology extractor 10 and applies the topological rules according to the topology. The label generator 20 assigns labels in accordance with the vessel classifications found to comply with the rules. The rules allow the label generator to ignore any illegal (anatomically incorrect) label assignments, thereby optimising the label assignment by reducing the number of labels that can be legally assigned to any segment. For the simple seven-segment tree shown in FIG. 4 and the above example label pool, there are 2,079,152 ($8^7$) combinations of labels and segments. Application of the topological rules reduces this number to just 511 legally labeled polyline trees. These are produced by considering the topology of the original tree, without using any information about the physical structure of the arterial tree of interest.

Thus, the label generator produces a set of labeled candidate polyline trees 2, each of which is labeled with anatomically feasible labels according to the topology of the original unlabeled polyline tree 1.

Figure 5:
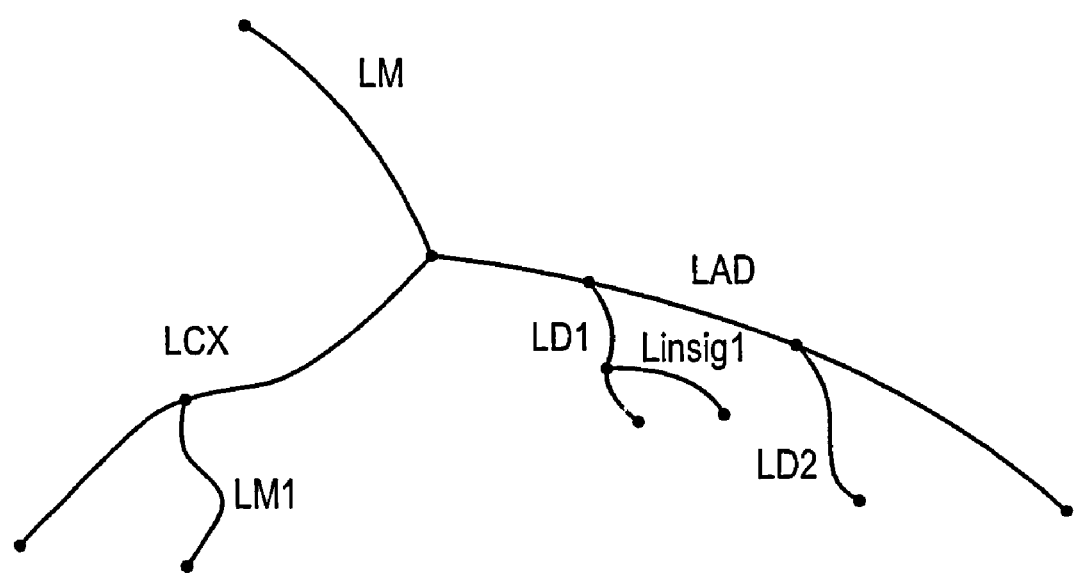
FIG. 5 shows an example of a polyline tree with anatomical labels showing the classification of the vessels within the tree.

FIG. 5 shows an example of a labeled polyline tree.

In order to reduce the number of candidate labeled trees in the set produced by the label generator 20 and the topology checker 24, it is proposed to filter the candidates according to the physical structure and spatial characteristics of the arterial tree under consideration. To achieve this, the candidate topologically feasible labeled trees are supplied to a geometry checker 30. The geometry checker operates by considering the classification of each vessel/segment in each labeled tree, and determining if this classification is valid according to a set of geometric rules, said geometric rules determined according to known physical and spatial features of coronary arterial trees. Any invalid classification results in the elimination of that labeled tree from the candidate set.

In this particular embodiment, only the physical characteristics pertaining to the centrelines of the vessels, and which can therefore be obtained from the polyline tree, are considered. Thus, attributes such as vessel diameter are disregarded. This has been found to be adequate for reducing the size of the candidate set. However, physical attributes which are obtainable from the original image data, such as vessel diameter, can be considered if desired.

The physical characteristics derivable from the polyline tree refers to the linear dimensions and absolute spatial positions of the segments (in contrast to the relative generational positions within the tree indicated by the topology). Thus, vessel length, distance from other vessels and branching points, and whether a vessel's spatial position is to the left, the right, anterior or posterior are considered.

The geometry checker 30 receives each fully-labeled candidate tree, applies geometric rules unique to the various classes of vessel and relevant to fully-labeled trees (rules in the category of "if a segment is labeled as X, any related segment labeled as Y must have particular characteristics"), and rejects a candidate if its labels do not comply with the rules.

In this embodiment, the geometric rules are:
For the LAD
Looking in the direction going down the vessel, all LDS must exist on the right side of the vessel and LINSIGs must be on the right.
For the LCX
The vessel must traverse a direction posterior to its initial sibling (normally the LAD).
For every occurring LMG, there must be an LCX segment as a sibling;
Looking down the LCX, all LMG vessels must be on the left side and any vessels coming off the right side must be LINSIG.
The LCX always starts within a given distance from the root of the left coronary tree.
For the LRI:
LRI vessels can only be present when the LAD and LCX are present.
LRI vessels must be in-between the LAD and LCX proximal segments.
For the RCA:
RCA segments can only begin within a given distance from the root of the right coronary tree.
For the RPD:
RPD can only have RINSIG as a sibling.

The geometric rules are stored in memory accessible by the geometry checker, which may be external memory or memory located within the geometry checker, depending on the hardware and/or software configuration used to implement the system.

Application of such geometric rules can dramatically reduce the size of the candidate set. For example, for the seven-segment tree in FIG. 4, the 511 topologically-feasible candidate labeled trees output by the label generator 20 can be reduced to about 71 geometrically-feasible candidate labeled trees by the geometry checker 30. All labeled candidates not eliminated by the geometry checker 30 are output as a set of geometrically-feasible labeled candidate trees 3.

Important differences between the operation of the geometry checker 30 and the label generator 20/topology checker 24 are that the geometry checker takes in a fully labeled polyline tree as input while the topology checker takes in an unlabeled predecessor array or other topological representation as input, and the geometry checker filters using spatial rules while the topology checker filters based on positional rules.

The set of geometrically-feasible labeled trees 3 output by the geometry checker 30 is passed to the merit function module 40. This module operates to calculate a figure of merit for each candidate labeled tree in the set 3, and outputs the labeled tree 4 with the best figure of merit.

In an embodiment, the figure of merit is calculated by first determining a so-called "feature vector" for each segment in the labeled tree. The feature vector is a numerical descriptor of a vessel which is calculated from measurements of a preselected set of characteristics or features of the segment and its corresponding vessel, where some measurements are determined from the polyline tree and some from the original image data. Thus, each segment of the polyline tree now has a feature vector. For each labeled segment in a candidate tree, the feature vector for that segment is compared with a mean feature vector and a variance-covariance matrix previously determined (discussed further below) for a vessel of the anatomical class indicated by the segment's label. In this embodiment, the comparison is performed so as to determine a log-likelihood for the labeled segment. Log-likelihood measures the closeness of test data (in this case the candidate labeled segments) to distributions of known data by considering a variance-covariance matrix. When the log-likelihoods have been determined for every segment in the labeled tree, the log-likelihoods are combined together, and the resulting value is taken as the figure of merit for that labeled tree. In a simple embodiment, the log-likelihoods may be summed to produce the figure of merit. Alternatively, a weighted sum may be used, or the log-likelihood may be normalized by multiplication with the proportional length of each vessel.

This is repeated for every candidate labeled tree in the set 3. The figures of merit are then compared and the labeled tree with the best figure of merit is identified. Depending on how the numerical values of the feature vectors, the log-likelihoods and the figures of merit are defined and handled, the best figure of merit may be the highest figure or the lowest figure.

This identified tree 4 is output by the merit function module as the final labeled tree, with each segment of the tree classified into an anatomical class which is indicated by its assigned label, the anatomical class being the class of the corresponding vessel in the originally imaged coronary artery tree. The labels can be used as required, for example to enable the display of text labels on a displayed image of the original image data, or as an input together with the image data to a piece of diagnostics or training software.

The purpose of the log-likelihood is to indicate how well the features of the vessel in question correspond to the features of a vessel which is known to be of the vessel type into which the vessel in question has been classified. It is an indication of how probable or likely it is that the vessel in question really is a vessel of the type indicated by its assigned label. It is therefore possible to use other probability functions in place of the log-likelihood, if desired.

Further, since the figure of merit aims to indicate the overall probability that each label within a candidate labeled tree is correct, other measures of comparison between a candidate tree and known correctly labeled trees may be used to determine the likely level of "correctness", this level being used as the figure of merit. Other suitable techniques for obtaining a likelihood or probability measure for a labelled tree include K-nearest neighbour, Baysian histograms and variance-covariance matrices. As appropriate to the technique, the mean feature vectors and variance covariance matrices mentioned above are replaced by other suitable parameters derived from selected features of each anatomical class of vessel.

In the present embodiment, the merit function module is enabled to operate by being provided with mean feature vectors and variance-covariance matrices for each anatomical class of vessel in a coronary artery tree. A mean feature vector and a variance-covariance matrix is provided for each anatomical class or vessel type which is included in the label pool, giving a set of mean feature vectors and variance-covariance matrices. The mean feature vectors and variance-covariance matrices are obtained by implementing a training stage using image data which includes vessels which are known to be correctly classified or identified. The training stage may be carried out separately from the system used to automatically label the unlabeled tree, with the thus obtained set of mean feature vectors and variance-covariance matrices being provided to the merit function module in a data storage area. Alternatively, the labeling system can be implemented so as to be operable to perform the training stage, with the mean feature vectors and variance-covariance matrices being stored for subsequent use by the merit function module. In such an arrangement, a training stage can be run as an isolated process before the system is used to perform labeling. Alternatively, the training stage can be ongoing, with newly obtained correctly labeled image data sets being input to the system as they become available, to allow the mean feature vectors and variance-covariance matrices to be updated. These newly obtained labeled data sets may be externally obtained. Alternatively, some or all of the labeled trees output by the merit function module may be fed back into the system for update of the mean feature vectors and variance-covariance matrices.

Operation of the training stage will now be described, with reference to the upper part of the system shown in FIG. 2.

As shown in FIG. 2, in this embodiment the training stage is performed using a feature extractor 50 and a multi-variate Gaussian classifier 60. Correctly labeled coronary artery image data are used for training, and the feature extractor 50 receives as input a correctly labeled polyline tree 5 and its corresponding arterial tree image data 6 (which may or may not be segmented from its original volume data set). The polyline tree 5 is obtained from the image data 6 as described above with regard to the unlabeled polyline tree 1 which is input to the topology extractor 10.

The feature extractor 50 operates to extract certain vessel measurements and parameters from the polyline tree 5 and the image data 6. As many or as few vessel characteristics can be used for this purpose as required, depending on the level of accuracy required of the vessel classification and the amount of processing which it is desired or convenient to perform. According to one embodiment, the following features are measured:

Vessel segment length.

Vessel segment proximal diameter (this is the only feature which cannot be measured from the polyline tree and which therefore requires use of the image data).

Relative angles to parent vessel segment.

Vessel segment tortuosity.

Distance of the vessel segment start point from the root of the tree.

X-, y- and z-directions of the endpoint of each vessel segment;

Vessel segment length rank.

For a particular vessel, the feature measurements are combined to obtain a feature vector for that vessel. The feature vector is then stored together with the anatomical class (label) of the vessel. This is repeated to obtain feature vectors for some or all of the vessels/segments in the polyline tree 5.

Once all the required feature data has been extracted from all image data set, a new image data set 6 and polyline tree 5, again with known correct labels, are input to the feature extractor 10, and the feature vectors calculated and saved.

This process hence generates a set of training data, comprising, for each anatomical class or label (vessel type), a quantity of feature vector values. This training data 7 is supplied to the classifier 60.

When the training stage is being carried out, the classifier 60 operates in a training mode. It takes the input training data, and for each anatomical class it calculates a mean feature vector and a variance-covariance matrix for that class, using the plurality of feature vector values derived from the various labeled image data sets used for training. These are stored as a set of mean feature vectors and variance-covariance matrices, one for each anatomical class. Also, the classifier 60 may choose to determine the variance-covariance matrix pooled over all the classes (although other manipulations of the variance-covariance matrix aimed at increasing classifier accuracy may be used instead). The use of a pooled covariance matrix (rather than per class covariance matrices) leads to linear discriminate surfaces while reducing the number of parameters to be estimated, thereby reducing the required number of training sets.

The classifier 60 is also able to operate in a classification mode, when it operates in conjunction with the merit function module 40 for determination of the functions of merit of the candidate labeled trees 3. In the classification mode, it takes as input the calculated feature vectors for a candidate tree (which may, if desired, be determined using the feature extractor 50, rather than being determined within the merit function module as suggested above), and uses this data together with the stored mean feature vectors and variance-covariance matrix to calculate the log-likelihood for each segment in the candidate tree, from which the figure of merit for that tree is calculated. The figure of merit can be calculated by the classifier 60 or by the merit function module 40. In more detail, the operation of the classifier 60 in an embodiment of the classification mode comprises the following steps:

The classifier takes as input the measured feature vector for each vessel, z and uses the mean feature vector and variance-covariance matrix for each classification of the vessel to calculate the log-likelihood for each class;

The log-likelihood is proportional to the probability of observing the measured feature vector z, given the class $w_k$ (know as likelihood).

$P(z|w_k)=1/(\sqrt{(2\pi)^N|C|})\exp((-\frac{1}{2})*(z-\mu_k)^T C^{-1}(z-\mu_k))$ By applying Bayes' theorem, the posterior probability, i.e. the probability of a vessel belonging to class $w_k$, given its measurement vector z is given by:

$P(w_k|z)=P(w_k)*P(z|w_k)/P(z)$ where $P(w_k)$ is the prior probability of observing the class $w_k$.

Equal priors are assumed in this case and therefore the posterior probability becomes equivalent to the likelihood.

The log-likelihood is used as a measure of merit.

As described thus far, the method for automatic labeling of coronary artery image data proposes that the data, after conversion to a polyline tree, is first filtered according to its topological features, and then filtered according to its physical features, before determination of a figure of merit for each of the resulting candidate labeled polyline trees. This approach has been found to be efficient at reducing the total number of candidates and accurate in identifying the correctly labeled tree. However, the technique may be adapted such that the geometric filtering is carried out first, followed by the topological filtering. Alternatively, if a simpler system is desired at the cost of potentially longer processing time and possible reduced accuracy, one or the other of topological filtering and geometrical filtering may be used without the other.

The system shown in FIG. 2 may be implemented using any combination of hardware or software. While the system has been illustrated and described in terms of a plurality of modules, the functionality of each module may be implemented using software or hardware, and the functionality of more than one module may be combined into a single module, or divided between modules other than in the combination illustrated in FIG. 2.

Also, the system may, if desired, be integrated into a hospital PACS network. In this way, the raw image data can be recorded by an appropriate three-dimensional imaging apparatus connected to the network, and stored to an image database together with associated data such as patient data and the like (for example using the DICOM standard file format), from which it can be retrieved and delivered to a workstation on the PACS network for processing and viewing by a clinician, including processing according to an embodiment of the present invention. The resulting classified and labeled image data can be stored back into the database for subsequent use if desired.

Although the invention has been described with specific reference to the automatic classification and labeling of coronary artery tree image data, it can be adapted for processing of image data of other tree-like anatomical structures having definable topological and geometric characteristics. Appropriate rule sets and label pools can be defined for such applications.

REFERENCES

[1] N Ezquerra et al, "IEEE Transactions on Medical Imaging", vol. 17, pp 429-441, 1998

[2] E Bengoetxea, "Inexact graph matching using estimation of distribution algorithms", PhD thesis from Ecole Nationale Supérieure des Télécommunications, 2002

[3] S Bouix et al, "Medical Image Analysis", vol. 9, pp 209-221, 2005

[4] Thomas H Cormen et al, "Introduction to Algorithms", second edition, MIT Press, ISBN 0262032937, 2001

What is claimed is:

1. A method of automatically classifying anatomical features shown in a medical image volume data set, the method comprising:

obtaining a polyline tree comprising a plurality of connected points in the data set corresponding to the centrelines of vessels in an arterial tree imaged in the data set, each vessel in the arterial tree being represented by a segment in the polyline tree;

forming a topological representation of the polyline tree which indicates the relative generational positions of the segments within the polyline tree;

comparing the topological representation with a set of topological rules specifying anatomically permissible relative generational positions of vessels in an arterial tree to identify feasible anatomical classifications for the vessels represented by each segment in the polyline tree;

generating a set of candidate labeled polyline trees by associating labels representing the identified anatomical classifications with the corresponding segments in the polyline tree, each candidate labeled polyline tree being one combination of the identified feasible anatomical classifications;

comparing each candidate labeled polyline tree with a set of geometric rules specifying anatomically permissible spatial attributes of vessels in an arterial tree which can be determined from a polyline representation and rejecting any candidate having one or more labels representing vessels which do not comply with the geometric rules;

calculating a figure of merit for each remaining candidate labeled polyline tree by comparing features of the vessels represented in the polyline tree with known features of vessels in the anatomical classes indicated by the labels associated with the segments representing the vessels to determine a probability of the correctness of the labels in each candidate, the figure of merit reflecting the probability; and identifying the candidate labeled polyline tree having the best figure of merit.

2. A method according to claim 1, in which the topological representation comprises a predecessor array.

3. A method according to claim 1, further comprising associating the labels from the identified candidate with the corresponding vessels in the imaged arterial tree to indicate the classification of the vessels.

4. A method according to claim 1, in which calculating a figure of merit for each remaining candidate labeled polyline tree comprises:

measuring a set of preselected features of each vessel represented in the polyline tree;

combining the measurements for each vessel to calculate a feature vector for each vessel; and for each candidate labeled polyline tree, comparing the calculated feature vector for each vessel with one or more predetermined parameters derived from features of the anatomical class of vessel indicated by the label associated with the segment representing that vessel to determine a probability that each label is correct, and combining the probabilities within each candidate labeled polyline tree to produce a figure of merit for each candidate.

5. A method according to claim 4, in which the predetermined parameters comprise a mean feature vector and a variance-covariance matrix for the anatomical class of vessel.

6. A method according to claim 5, in which comparing the calculated feature vector for each vessel with a predetermined mean feature vector and a variance-covariance matrix to determine a probability comprises calculating a log-likelihood.

7. A method according to claim 6, in which combining the probabilities to produce a figure of merit comprises summing the log-likelihoods for every labeled segment in the candidate labeled polyline tree.

8. A method according to claim 5, in which the predetermined mean feature vectors are the mean values of a plurality of feature vectors calculated for correctly classified vessels in arterial trees imaged in other data sets and the variance-covariance matrices are calculated for correctly classified vessels in arterial trees imaged in the other data sets.

9. A method according to claim 4, in which comparing the calculated feature vector for each vessel with one or more parameters derived from features of the anatomical class of vessel indicated by the label associated with the segment representing the vessel comprises use of a K-nearest neighbour technique.

10. A method according to claim 4, in which comparing the calculated feature vector for each vessel with one or more parameters derived from features of the anatomical class of vessel indicated by the label associated with the segment representing the vessel comprises use of Baysian histograms.

11. A method according to claim 4, in which measuring the preselected features for each vessel comprises measuring features from the polyline tree and from the data set.

12. A medium storing a computer program product operable to cause a computer system to implement the method according to claim 1.

13. A system for automatically classifying anatomical features shown in a medical image volume data set, the system comprising:
a computer;
a topology extractor module operable to receive a polyline tree comprising a plurality of connected points in the data set corresponding to the centrelines of vessels in an arterial tree imaged in the data set, each vessel in the arterial tree being represented by a segment in the polyline tree, and to form a topological representation of the polyline tree which indicates the relative generational positions of the segments within the polyline tree;
a memory having stored thereon a set of topological rules specifying anatomically permissible relative generational positions of vessels in an arterial tree;
a set of labels representing anatomical classifications of arterial vessels;
a topology checker module operable to compare the topological representation with the set of topological rules to identify feasible anatomical classifications for the vessels represented by each segment in the polyline tree and to generate a set of candidate labeled polyline trees by associating labels from the label set which represent the identified anatomical classifications with the corresponding segments in the polyline tree, each candidate labeled polyline tree being one combination of the identified feasible anatomical classifications;
a set of geometric rules specifying anatomically permissible spatial attributes of vessels in an arterial tree which can be determined from a polyline representation;
a geometry checker module operable to compare each candidate labeled polyline tree with the set of geometric rules and reject any candidate having one or more labels representing vessels which do not comply with the geometric rules; and
a merit figure module operable to calculate a figure of merit for each remaining candidate labeled polyline tree by comparing features of the vessels represented in the polyline tree with known features of vessels in the anatomical classes indicated by the labels associated with the segments representing the vessels to determine a probability of the correctness of the labels in each candidate,
the figure of merit reflecting the probability, and to identify the candidate labeled polyline tree having the best figure of merit.

14. A system according to claim 13, in which the topological representation comprises a predecessor array.

15. A system according to claim 13 in which the merit figure module is further operable to associate the labels from the identified candidate with the corresponding vessels in the imaged arterial tree to indicate the classification of the vessels.

16. A system according to claim 13, further comprising a set of predetermined parameters derived from features of anatomical classes of vessel, calculated from measurements of features of correctly classified vessels in arterial trees in image volume data sets; and in which:
the merit figure module is operable to calculate a figure of merit for each remaining candidate labeled polyline tree by:
measuring a set of preselected features of each vessel represented in the polyline tree;
combining the measurements for each vessel to calculate a feature vector for each vessel; and
for each candidate labeled polyline tree, comparing the calculated feature vector for each vessel with one or more of the parameters for the anatomical class of vessel indicated by the label associated with the segment representing that vessel to determine a probability that each label is correct, and combining the probabilities within each candidate labeled polyline tree to produce a figure of merit for each candidate.

17. A system according to claim 16, in which the predetermined parameters comprise a mean feature vector and a variance-covariance matrix for each anatomical class of vessel.

18. A system according to claim 17, in which the merit figure module is operable to compare the calculated feature vector for each vessel with a mean feature vector and variance-covariance matrix to determine a probability by calculating a log-likelihood.

19. A system according to claim 18, in which the merit figure module is operable to combine the probabilities to produce a figure of merit by summing the log-likelihoods for every segment in the candidate labeled polyline tree.

20. A system according to claim 17, in which the mean feature vectors are the mean values of a plurality of feature vectors calculated for correctly classified vessels in arterial trees imaged in a plurality of volume data sets and the variance-covariance matrices are calculated for correctly classified vessels in arterial trees imaged in the plurality of volume data sets.

21. A system according to claim 17, further comprising:
a feature extractor and classifier module operable to:
    measure sets of preselected features of correctly classified vessels in a plurality of polyline trees representing a plurality of imaged arterial trees;
    combine the measurements for each vessel to calculate a feature vector for each vessel; and
    calculate a mean feature vector and a variance-covariance matrix for each anatomical class of vessel from the calculated feature vectors; and
memory operable to store the mean feature vectors and variance-covariance matrices for retrieval by the merit figure module when calculating figures of merit.

22. A system according to claim 16, in which the merit figure module compares the calculated feature vector for each vessel with one or more of the parameters for the indicated anatomical class of vessel by use of a K-nearest neighbour technique.

23. A system according to claim 16, in which the merit figure module compares the calculated feature vector for each vessel with one or more of the parameters for the indicated anatomical class of vessel by use of Baysian histograms.

24. A system according to claim 16, in which the preselected features for each vessel are measured from the polyline tree and/or from the data set.

* * * * *